US010279145B2

(12) United States Patent
Meddings et al.

(10) Patent No.: US 10,279,145 B2
(45) Date of Patent: May 7, 2019

(54) CATHETER PLACEMENT ASSIST DEVICE AND METHOD OF USE

(71) Applicant: THE REGENTS OF THE UNIVERSITY OF MICHIGAN, Ann Arbor, MI (US)

(72) Inventors: Jennifer Meddings, Ann Arbor, MI (US); John O. Delancey, Ann Arbor, MI (US); James A. Ashton-Miller, Ann Arbor, MI (US); Dee E. Fenner, Ann Arbor, MI (US); Sanjay Saint, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/055,390

(22) Filed: Aug. 6, 2018

(65) Prior Publication Data

US 2018/0339133 A1    Nov. 29, 2018

Related U.S. Application Data

(63) Continuation of application No. PCT/US2017/033553, filed on May 19, 2017.
(Continued)

(51) Int. Cl.
*A61B 46/00*    (2016.01)
*A61M 25/01*    (2006.01)
(Continued)

(52) U.S. Cl.
CPC ......... *A61M 25/0111* (2013.01); *A61B 46/30* (2016.02); *A61B 90/40* (2016.02);
(Continued)

(58) Field of Classification Search
CPC .......... A61M 25/0111; A61M 25/0017; A61M 2210/1092; A61M 25/01;
(Continued)

(56) References Cited

U.S. PATENT DOCUMENTS 3,422,817 A * 1/1969 Mishkin .............. A61M 16/047
                                                   128/207.14
3,512,185 A * 5/1970 Ellis ........................ A61F 5/455
                                                       4/144.3
(Continued)

FOREIGN PATENT DOCUMENTS

DE          10060088 A1    7/2002
WO     WO-2016/116915 A1    7/2016

OTHER PUBLICATIONS

International Application No. PCT/US17/33553, International Search Report and Written Opinion, dated Aug. 22, 2017.

*Primary Examiner* — Adam Marcetich
(74) *Attorney, Agent, or Firm* — Marshall, Gerstein & Borun LLP (57) ABSTRACT

A single-use, sterile, disposable catheter placement assist device to aid in the sterile placement of transurethral urinary catheters in female patients, and a method for catheter placement using the device. The catheter placement assist device includes a labia separator with flared wings having a curved profile. The wings meet at a valley. The catheter placement assist device also includes a posterior shield that covers the perineal tissues including the anus to prevent contamination of the sterile catheter with bacteria and may further include a spout that may be shallowly inserted into the vagina to position the catheter device to optimize labial separation, retraction of the posterior vaginal wall, perineal shielding, and visualization of the urethral meatus. The additional features of a light, a handle, a catheter tip holder, (Continued)

a swab storage location, and a stackable configuration may further be included with the catheter placement assist device.

20 Claims, 7 Drawing Sheets

Related U.S. Application Data (60) Provisional application No. 62/339,295, filed on May 20, 2016.

(51) Int. Cl.
*A61B 90/40* (2016.01)
*A61M 25/00* (2006.01)
*A61B 46/23* (2016.01)

(52) U.S. Cl.
CPC ....... *A61M 25/01* (2013.01); *A61B 2046/234* (2016.02); *A61M 25/0017* (2013.01); *A61M 2025/0191* (2013.01); *A61M 2210/1092* (2013.01)

(58) Field of Classification Search
CPC .......... A61M 2210/1475; A61M 25/02; A61B 46/30; A61B 2046/234; A61B 10/007; A61B 2010/0074; A61B 10/0045; A61B 1/303; A61B 1/307; A61B 1/32; A61F 5/4556
See application file for complete search history.

(56) References Cited

U.S. PATENT DOCUMENTS

| | | | |
|---|---|---|---|
| 3,583,388 A * | 6/1971 | Hovick | A61B 10/007 600/574 |
| 3,683,911 A * | 8/1972 | McCormick | A61M 25/02 128/DIG. 26 |
| 3,796,214 A * | 3/1974 | Davis | A61B 1/32 600/205 |
| 3,815,581 A | 6/1974 | Levin | |
| 4,610,675 A * | 9/1986 | Triunfol | A61F 5/4401 4/144.3 |
| 4,615,692 A * | 10/1986 | Giacalone | A61F 5/455 600/574 |
| 4,815,151 A * | 3/1989 | Ball | A61F 5/4556 4/144.1 |
| 4,936,838 A * | 6/1990 | Cross | A61F 5/455 600/574 |
| 5,084,036 A * | 1/1992 | Rosenbaum | A61M 25/01 604/329 |
| 5,295,983 A * | 3/1994 | Kubo | A61F 5/455 4/144.3 |
| 5,520,675 A * | 5/1996 | Knox-Sigh | A61F 13/47209 604/385.17 |
| 6,074,380 A * | 6/2000 | Byrne | A61M 25/0111 604/174 |
| 6,571,395 B1 * | 6/2003 | Korkor | A41D 13/1245 2/104 |
| 6,875,200 B1 * | 4/2005 | Ajagbe | A61F 13/148 602/41 |
| 7,104,980 B1 | 9/2006 | Laherty et al. | |
| 8,202,263 B2 | 6/2012 | Feloney | |
| 2003/0073998 A1 * | 4/2003 | Pagliuca | A61B 17/0218 606/86 A |
| 2006/0100607 A1 | 5/2006 | Brown | |
| 2010/0256580 A1 * | 10/2010 | Faber | A61M 25/0017 604/329 |
| 2014/0303447 A1 | 10/2014 | Singh et al. | |
| 2016/0325075 A1 | 11/2016 | Madigan et al. | |
| 2016/0331599 A1 * | 11/2016 | Saitoh | A61G 9/00 |

* cited by examiner

CATHETER PLACEMENT ASSIST DEVICE AND METHOD OF USE

CROSS REFERENCE TO RELATED APPLICATIONS

This application claims the benefit of the filing date of U.S. Provisional Patent Application No. 62/339,295, filed May 20, 2016, entitled "Catheter Placement Device and Method of Use." The entire contents of U.S. Provisional Application No. 62/339,295 is hereby incorporated by reference.

This application is a continuation application based on PCT Application No. PCT/US17/33553, filed on May 19, 2017 and entitled "Catheter Placement Device and Method of Use", the contents of which is incorporated herein by reference in its entirety.

STATEMENT OF GOVERNMENT INTEREST

This invention was made with government support under AG024824 awarded by the National Institutes of Health. The government has certain rights in the invention.

FIELD OF THE DISCLOSURE

This application describes a catheter placement assist device for assisting aseptic placement of a Foley urinary catheter for female patients. This device will assist aseptic placement of indwelling transurethral urinary catheters (commonly known as "Foley catheters") and intermittent straight catheters.

BACKGROUND

Urinary catheters are the most commonly used biomedical device, with approximately one in every five patients admitted to an acute care hospital receiving an indwelling catheter; the rate of catheter use is even higher among Medicare patients. Foley catheters are soft, plastic or rubber tubes that are placed transurethrally into the bladder to provide continuous drainage and relief when there is urinary retention, to monitor urine output for critically ill patients, to manage urination during surgery, and to provide end-of-life care. Foley catheters are commonly placed in hospital settings (emergency rooms, wards, intensive care units (ICUs), and operating rooms), urology and gynecology clinic settings, and in nursing homes. Foley catheters are recommended in the following situations: when urine is blocked due to bladder stones, blood clots in the urine, or narrowing of the urethra; during surgery of the prostate gland or in the genital area, such as a hip fracture repair or hysterectomy; after injury to the nerves of the bladder; spinal cord injury; when a condition impairs one's mental function, such as dementia; and when medications are taken that impair the ability of one's bladder muscles to squeeze, which causes urine to remain stuck in the bladder. Intermittent straight catheters (ISCs) are catheters that are commonly used in females with chronic bladder emptying issues due to neurologic conditions (such as multiple sclerosis) and pelvic floor muscle disorders. ISCs are inserted to drain the bladder, then immediately removed. Both indwelling Foley catheters and ISCs are associated with an increased rate of infection, and are placed using the same sterile procedure by clinicians in hospitalized and ambulatory patients to reduce the risk of introducing bacteria into the bladder during the placement procedure.

Certain conditions can make it quite difficult to part the labia of the female genitalia for sterile insertion of a urinary catheter. For example, it is not uncommon for the labia to be much thicker than normal, as much as 10 cm, in women with morbid obesity. Women who are bed bound and who must chronically lie on one side of their body can develop asymmetric labia due to dependent edema (i.e., swelling) in the inferior labia due to poor lymphatic drainage. Yet others have congenital asymmetry or anasarca (i.e., severe swelling). All of these conditions can make it more difficult to avoid contamination of a sterile catheter.

One of the primary complications that arise from the procedure of Foley catheter placement is the introduction of bacteria to the patient in either the bladder or mucosal membranes and blood stream, resulting in catheter-associated urinary tract infection. Catheter-associated urinary tract infection (CAUTI) is the most frequent healthcare-associated infection in the United States. Although most cases of bacteriuria are asymptomatic and resolve spontaneously once the catheter is removed, as many as 30% of patients with catheter-associated bacteriuria will develop symptom-related urinary tract infections requiring treatment. Additionally, the most clinically important adverse outcome associated with bacteriuria is urinary tract-related bacteremia. Bacteremia, or sepsis, is a highly morbid and costly complication associated with hospitalization and can increase hospital length of stay, or require hospital readmissions in the event a patient has been discharged, the costs for which insurers are increasingly resistant to reimburse.

For the above-mentioned reasons, the placement of Foley catheters using sterile (aseptic) techniques is imperative. Unfortunately, it is extremely challenging to maintain sterility throughout the multi-step procedure required for placement, particularly in females. Maintaining sterility during catheter placement in women is difficult due to the anatomic location of the female urethra and the need for retraction of the external female genitalia (vulva) in conjunction with common medical comorbidities such as obesity, edema, osteoarthritis and acute medical conditions such as altered mental status. Although various technologies have been employed to reduce the risks and associated complications of indwelling urinary catheters, such as bladder irrigation and antibiotic-coated catheters, there is still a need to improve the sterility of catheter placement.

SUMMARY

The current disclosure is directed towards a single-use, sterile, disposable catheter placement assist device to aid in the sterile placement of transurethral urinary catheters in female patients. The catheter placement assist device includes a labia separator with flared wings on bilateral sides that meet in a valley that has one end serving as a spout, and the other end serving as a posterior shield. On either side, the wings continue out laterally past the spout to create an aperture and then overlap one another for a short distance before terminating. Alternately, instead of overlapping, a permanent gap may be provided on the anterior side of the aperture between the wings and medical grade adhesive tape may adhere the two sides of the gap together. The wings, valley, and spout are used to atraumatically retract the labia major and minora tissues, enabling better visualization and access through the introital aperture to the urethral meatus where a urinary catheter is to be placed. The wings, valley, spout, posterior shield, and aperture enable the sterile catheter to be inserted into the urethral meatus without becoming contaminated with bacteria by contact with the labia. During placement of the catheter placement assist device, the valley and spout of the catheter placement assist device follows the urogenital cleft into the vestibule. The spout does not extend past the hymenal ring of the vagina when the catheter placement assist device is in place. The wings have a curved profile that allows the labia minora to be parted and then, as the catheter placement assist device is pressed further proximally into the vestibule, part the labia majora. The angle at which the wings meet may decrease or increase non-linearly depending on user preference. The shape of the wings facilitates placement of the catheter placement assist device even in women having thick or asymmetric labia. In some arrangements within the scope of the present disclosure, the wings are moldable or malleable so that they can be shaped as necessary to accommodate labial asymmetry. Moldable wings may be made from a thermoplastic or elastic material, which can be warmed in water for molding and allowed to cool prior to use. Alternately, moldable wings may include metallic wire that can be bent to a desired shape. The metallic wire may be coated. The catheter placement assist device also includes a posterior shield that covers the perineal tissues including the anus to prevent contamination of the sterile catheter with bacteria, particularly gastrointestinal bacteria, from that area.

After the catheter is placed, the catheter placement assist device is removed from the patient by lifting it, separating the overlapping wings to create a space at the potential gap, and aligning space created at the potential gap with the body of the catheter so that the overlapping portion of the wings can be drawn past the catheter body thereby removing the catheter placement assist device and leaving the catheter in place. Alternately, in arrangements in which a permanent gap is provided between the wings that is spanned by medical grade adhesive tape, the tape is removed from the catheter placement assist device and the two sides of the gap can then be drawn past the catheter to remove the catheter placement assist device while leaving the catheter in place. In some arrangements, a space between the two sides of the permanent gap may always exist. In other arrangements, tension may be applied by the tape to the catheter placement assist device to close the permanent gap through deformation of the catheter placement assist device when the catheter placement assist device is placed. During removal, the two sides of the permanent gap may spring apart when the tape is removed to facilitate removing the catheter placement assist device while the catheter is in place.

Other arrangements of the device include the addition of a light, a handle, a catheter tip holder, and storage pocket or pouch for antimicrobial swabs. The catheter placement assist device may have a small light, such as a light-emitting diode (LED), to optimize visualization of the urethra for placement of a catheter. The catheter placement assist device may also have a small handle to assist initial placement, secure positioning, and to facilitate removal after catheter placement. In some arrangements within the scope of the present disclosure, the handle includes an end that may be rested against a bed surface, allowing the catheter placement assist device to be left in place for a few seconds with the wings on the inner surface of the labia and the handle acting as a monopod, so that, for example, a catheter can be picked up without the need for a second medical attendant. The handle itself may be bendable, extensible, or articulated with more than one part that can be extended and locked at an angle relative to one another. The catheter placement assist device may further include a catheter tip holder to hold the sterile catheter in a location to be readily accessible for the clinician placing the catheter. In addition, the catheter placement assist device may have a storage location, such as a pocket or pouch, for anti-microbial swabs to have them readily accessible for use for cleansing the vulvar skin to create the sterile field needed for urinary catheter placement. The catheter placement assist device may have a stackable configuration so that a plurality of catheter placement assist devices could be stacked on top of another within a small space, such as for shipping.

Benefits of the catheter placement assist device of the current disclosure include improved adherence to aseptic technique for female patients, fewer catheterization attempts needed before successful sterile placement of indwelling urinary catheter, improved patient comfort by reducing the number or duration of catheterization attempts required, and reduced rates of catheter-associated bacteriuria or infection, particularly for catheter-associated urinary tract infections occurring less than 48 hours after placement.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary arrangements, except as may be explicitly delineated in the corresponding written description. None of the drawings are necessarily to scale.

DETAILED DESCRIPTION

Figure 1A:
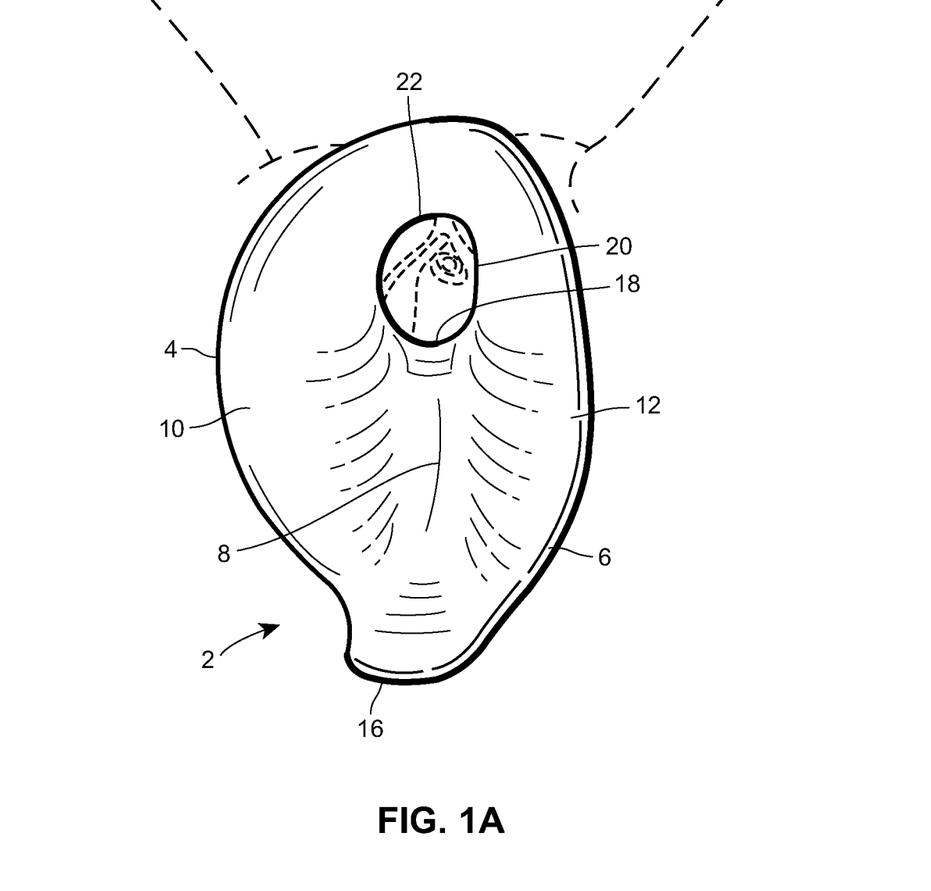
FIG. 1A illustrates a top view of an arrangement of a catheter placement assist device having overlapping wings.
Figure 1B:
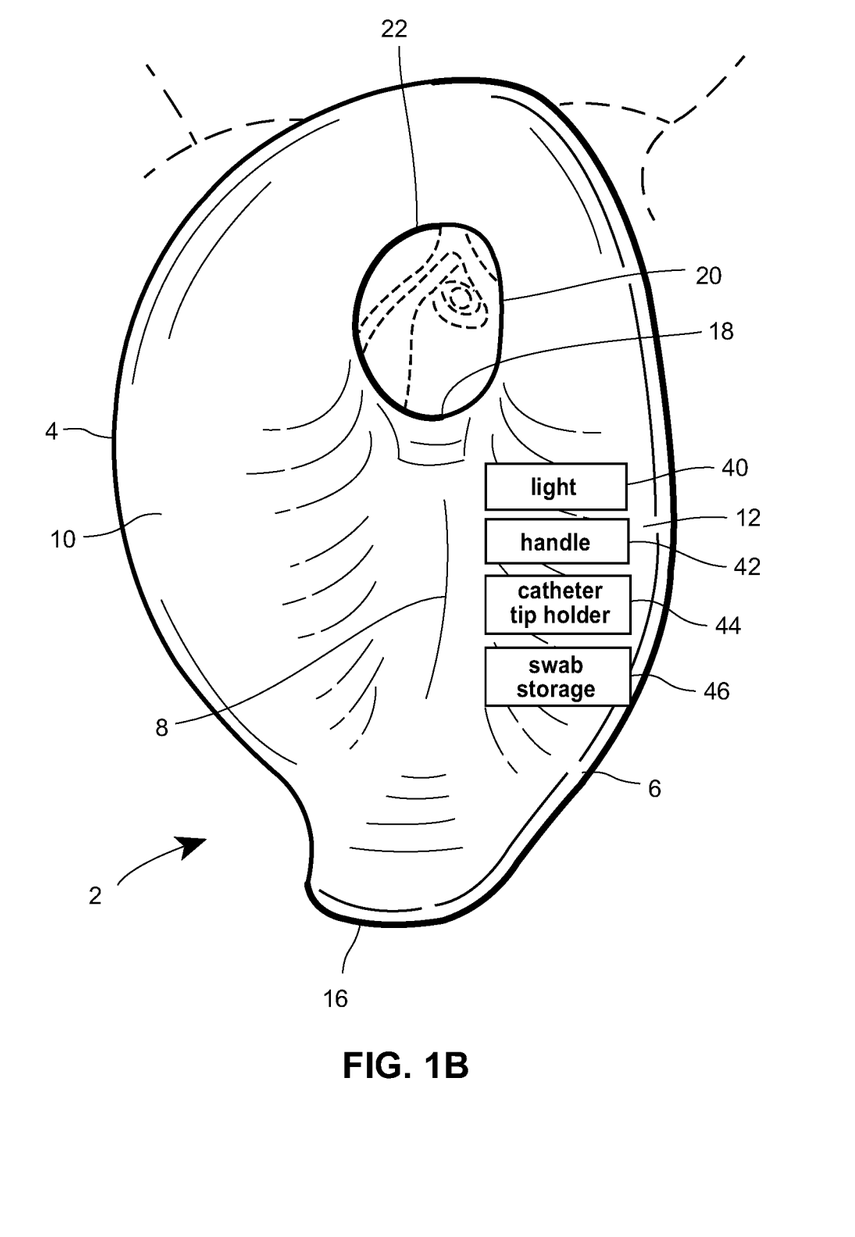
FIG. 1B is an enlarged view of the introital aperture of FIG. 1A.
Figure 2:
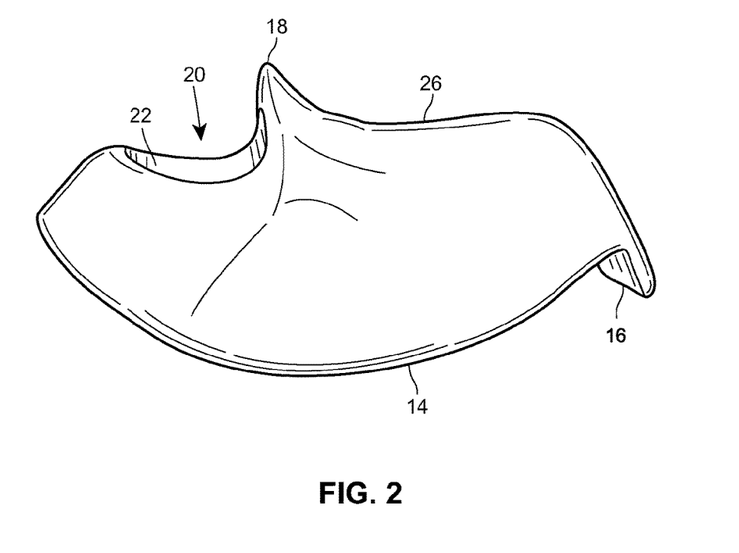
FIG. 2 illustrates a right side view of an arrangement of a catheter placement assist device.

Referring to the figures in detail, FIG. 1A illustrates a top view of a catheter placement assist device 2 as placed on an anatomic model of the female external perineal anatomy. FIG. 1B illustrates an enlarged view of the introital aperture 20 of the device depicted in FIG. 1A. FIG. 2 illustrates a right side view of the catheter placement assist device 2. In some arrangements, the overall three-dimensional shape of the catheter placement assist device 2 is formed so that a second catheter placement assist device 2 can be stacked on a first catheter placement assist device 2 and a third on the second and so on with little or no intervening empty space. This permits multiple stacked catheter placement assist devices 2 to be stored or shipped efficiently in small volumes.

The catheter placement assist device has two wings 4 and 6, each having a curved profile, that meet at a valley 8 located in the center of the device 2. As illustrated in FIG. 1, the wings 4 and 6 have clinician-facing surfaces 10 and 12 that are not in contact with the labia when the catheter placement assist device 2 is in position. As illustrated in FIG. 2, each wing 4 or 6 has a patient-facing surface 14 that is in contact with the labia when the catheter placement assist device 2 is in position. As illustrated in FIG. 1A, a posterior shield 16 extends from one end of the valley 8 at the base of the wings 4 and 6. The other end of the valley 8 forms a spout 18 for insertion into the vaginal vestibule. The spout 18 permits correct positioning of the catheter placement assist device 2 while also retracting labial tissue and the posterior vaginal wall to enable optimal visualization of the urethral meatus for insertion of the urinary catheter through the opening in the device called the introital aperture 20 that is formed by the spout 18 and the medial edges of bilateral extensions of the wings 4 and 6, which overlap one another before terminating. A potential physical gap 22, which may be spread to create a space, exists between the overlapping portions of the bilateral extensions of the wings 4 and 6.

FIG. 1B provides an enlarged view of the introital aperture 20 through which the urethral meatus is easily visualized to enable urinary catheter placement. The potential gap 22 permits removal of the catheter placement assist device 2 from the catheter after insertion of an indwelling urinary catheter by lifting the catheter placement assist device 2, separating the overlapping wings 4 and 6 to create a space at the potential gap 22, and aligning the axis of the space created at the potential gap 22 with the axis of the catheter body then pulling the overlapping wings 4 and 6 of the catheter placement assist device 2 past the body of the catheter. The catheter placement assist device 2 can then be discarded leaving the catheter in place.

In some arrangements within the scope of the present disclosure, the width of the catheter placement assist device 2 from the lateral edge of one wing 4 to the lateral edge of other wing 6 is approximately 3 inches, the length of the catheter placement assist device 2 from the posterior shield 16 to overlapping portion of the two wings 4 and 6 is 5 inches, and the depth of the catheter placement assist device 2 from the edge of each wing 4 or 6 to the tip of the spout 18 is about 1 inch. Other dimensions are possible and are considered within the scope of the present disclosure.

Additional features for other arrangements of the catheter placement assist device 2 include a light 40, a handle 42, catheter tip holder 44, and storage pocket or pouch for antimicrobial swabs 46, all shown schematically at 40 in FIG. 1B. A small light, which may be an LED, is mounted on the device to aide visualization of tissues in the introital aperture. A handle is used to help hold, insert, and remove the catheter placement assist device 2. In some arrangements within the scope of the present disclosure, the handle is bendable such that an end of the handle could be placed on a bed surface to temporarily secure the catheter placement assist device 2 in place. In other arrangements within the scope of the present disclosure, a catheter tip holder is used to store the sterile tip of the urinary catheter in a readily accessible location to use once the catheter placement assist device 2 is in optimal position. A storage location for antimicrobial swabs could be provided on the clinician-facing side of a flared wing.

FIG. 2 illustrates a right side view of the catheter placement assist device 2 of FIG. 1, showing the patient-facing surface of the flared wings 14, the patient-facing surface of the posterior shield 16, and spout 18. The spout 18 is shown for insertion into the vaginal vestibule, to position the catheter placement assist device 2 securely in order to optimally visualize the urethral meatus through the introital aperture 20 for urinary catheter insertion. The spout 18 is sized such that no portion of the catheter placement assist device 2 will pass the hymenal ring of the vagina.

Figure 3A:
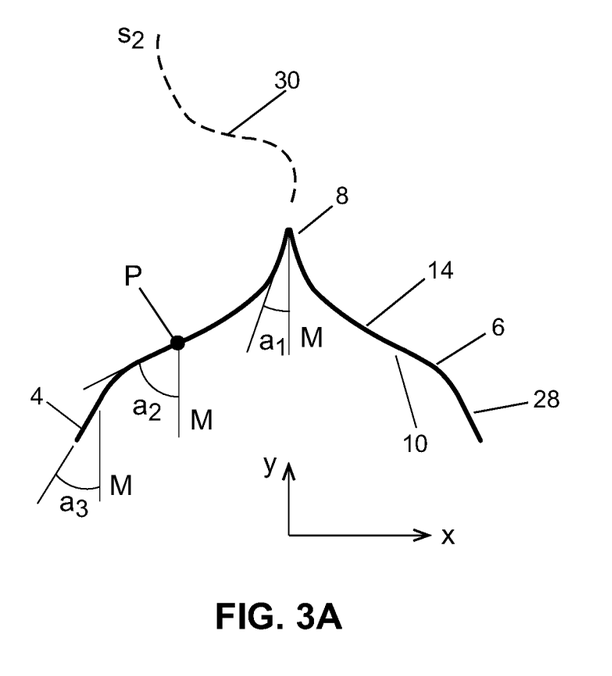
FIG. 3A illustrates a section taken through a catheter placement assist device orthogonal to and through its valley and a placement trajectory.
Figure 3B:
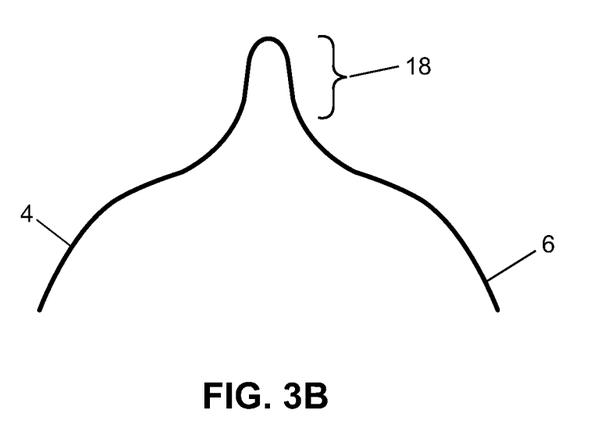
FIG. 3B illustrates a coronal section taken through the spout of a catheter placement assist device in a direction that is orthogonal to its valley.
Figures 3C, 3D:
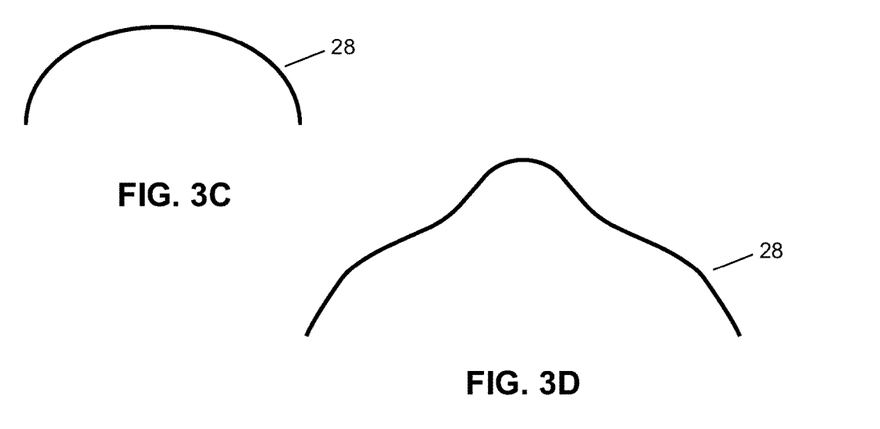
FIG. 3C illustrates a section taken through a catheter placement assist device in a direction that is orthogonal to its posterior shield.
FIG. 3D illustrates a section taken through a catheter placement assist device orthogonal to and through an alternatively shaped valley to that in FIG. 3A.
Figure 4:
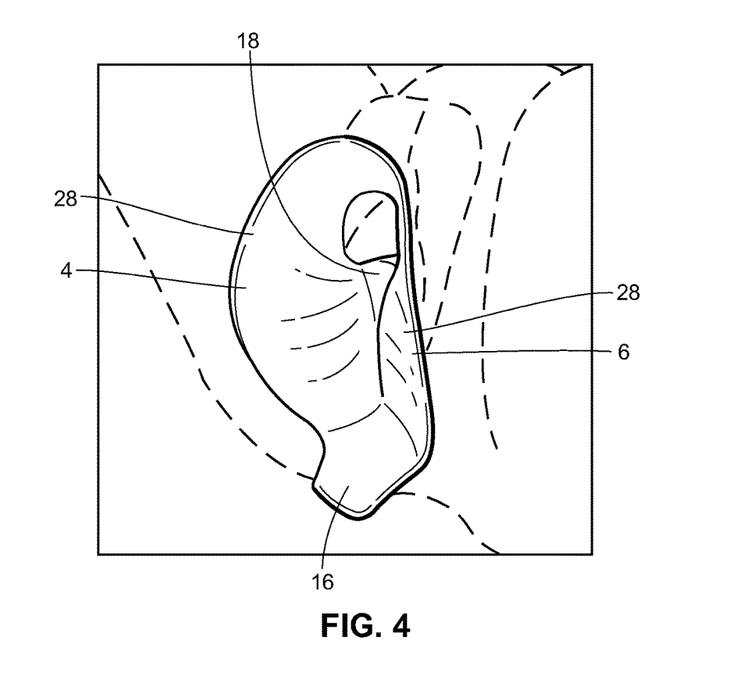
FIG. 4 illustrates the device at an angle to depict the curved wing profiles.

FIG. 3A illustrates a curved wing profile 28 of a catheter placement assist device 2 in the coronal plane through the valley 8 and a placement trajectory 30 using a diagram. An angle a (e.g., $a_1$ or $a_2$ or $a_3$) is determined for multiple surface points along the wings 4 and 6 by a tangent to a surface point P of a wing 4 or 6 and a midline M. The angle a increases and decreases non-linearly as one moves from the valley (8 in FIGS. 1A and 2) to the outside edge of a wing. During placement, the spout and valley (18 and 8 in FIG. 4, respectively) can be moved in the +y and +/−x directions to follow and enter a urogenital cleft with folds. For example, the spout 18 and valley 8 may travel placement trajectory from $s_1$ to $s_2$ in FIG. 3A as they part the labia minora and are pressed proximally into the vestibule. The movement of the valley 8 in the +/−x directions may be necessary to follow the urogenital cleft of women having asymmetric labia. FIG. 3B is a coronal section through the region of the spout. FIG. 3C illustrates a coronal plane section through the posterior shield 16. FIG. 3D illustrates an alternative curved wing profile 28 to that in FIG. 3A whereby the angle a decreases and then increases non-linearly and then decreases as one moves from the valley 8 to the outside edge of the wing. FIG. 4 uses a photograph to show this wing profile 28 placed with respect to female anatomy, depicting the flared wings 4 and 6, spout 18, and posterior shield 16 also depicted in FIGS. 1A and 1B.

Figure 5:
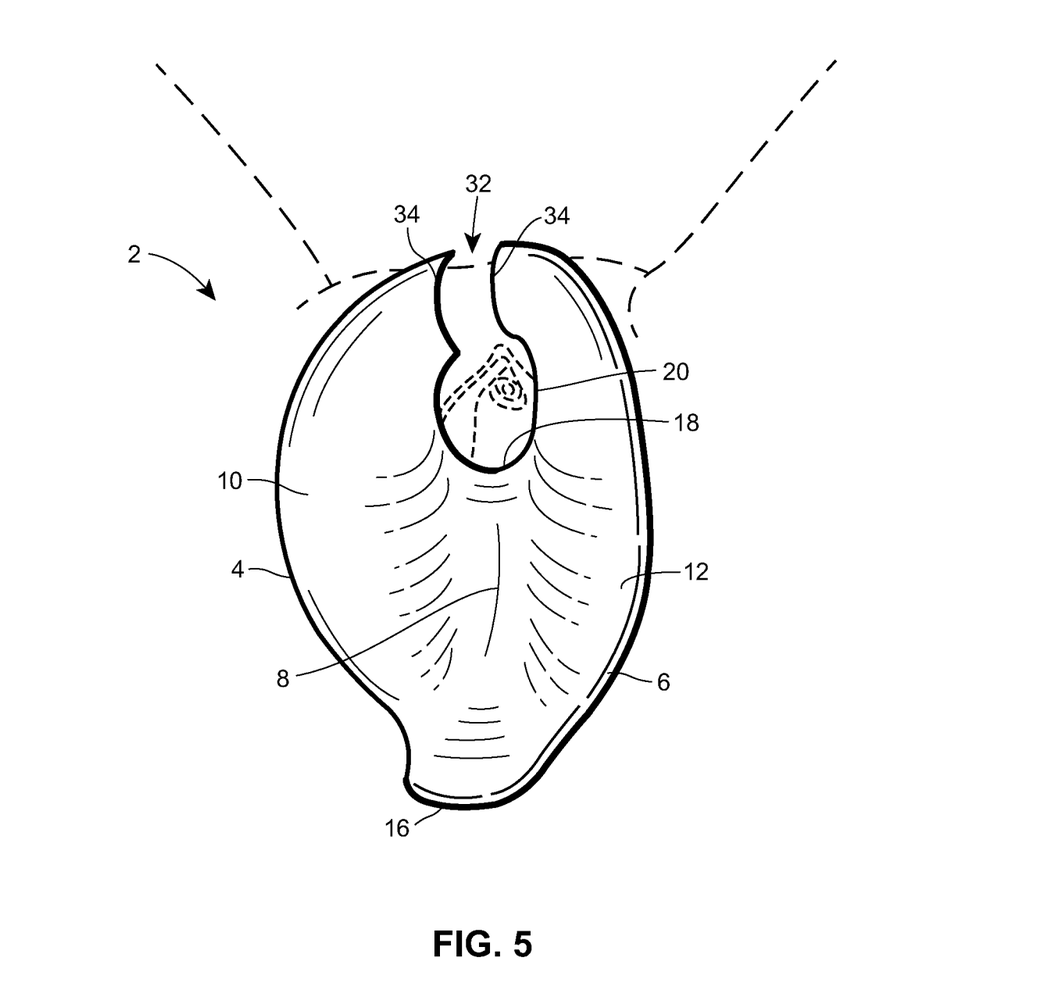
FIG. 5 illustrates a top view of an arrangement of a catheter placement assist device having a permanent gap between wings configured for connection between two sides of the gap by tape.

FIG. 5 depicts a catheter placement assist device 2 similar to that described with respect to FIGS. 1-4 except that wings 4 and 6 are configured such that a permanent gap 32 is provided adjacent to the introital aperture 20 on the anterior side of the introital aperture 20 when the catheter placement assist device 2 is in position before the wings 4 and 6 terminate. The permanent gap 32 has two sides 34. In some arrangements, the space between the two sides 34 may be approximately 1 cm. Other dimensions of the permanent gap 32 are possible and are considered within the scope of the present disclosure.

Figure 6:
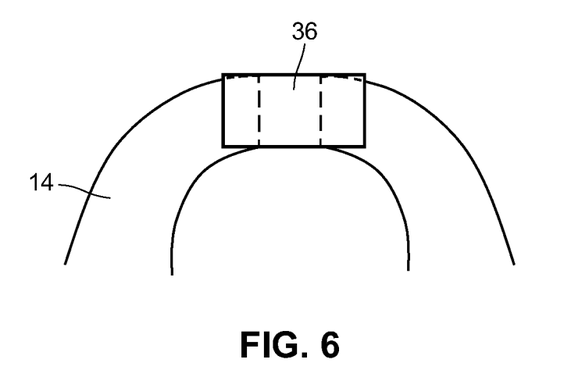
FIG. 6 illustrates a bottom view of the arrangement of FIG. 5 with a piece of tape spanning between the two sides of the gap.
Figure 7:
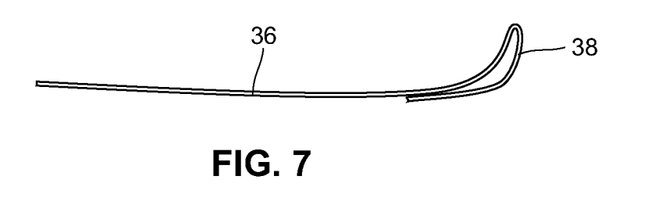
FIG. 7 illustrates a section taken through the tape depicting a tab provided on the tape.

As shown in FIG. 6, a piece of medical grade tape 36 is adhered to the patient-facing surface 14 and arranged to span the space between the two sides 34 of the permanent gap 32. The tape 36 prevents soft tissue from being pinched by inadvertently being caught in the permanent gap 32, which may have a space between the two sides 34 at all times. Adhering the tape 36 to the patient-facing surface 14 results in the smooth, non-adhesive side of the tape 36 facing the patient so as not to adhere to the patient's skin. In some arrangements, the tape 36 may include a tab 38 to facilitate grasping and removing the tape 32 from the patient-facing surface 14 prior to removing the catheter placement assist device 2. FIG. 7 shows a section taken through the tape 36 depicting the tab 38. In some alternate arrangements, the permanent gap 32 may be deformable and the space between the two sides 34 may be closed by adhering the tape 36 in tension between the two sides 34. In such alternate arrangements, upon tape 36 removal, the elastic nature of the catheter placement assist device 2 causes the permanent gap 32 to automatically open as the deformation induced by the closure of the permanent gap 32 is eliminated, thereby facilitating removal of the catheter placement assist device 2.

While various arrangements have been described herein, it will be understood that variations may be made thereto that are still within the scope of the appended claims.

What is claimed is:

1. A catheter placement assist device comprising:
   a pair of wings that meet at a valley, each of the wings having a curved profile;
   a spout protruding from one end of the valley, the spout forming one side of an introital aperture through which a urethral meatus can be optimally visualized;
   a posterior shield protruding from another end of the valley;
   wherein the wings overlap one another around the introital aperture before terminating.

2. The catheter placement assist device of claim 1, wherein the wings comprise at least one of a malleable material, an elastic material, and a malleable metallic wire.

3. The catheter placement assist device of claim 1, each of the wings having patient-facing surface that is positioned in contact with an inner side of the labia of a patient when the catheter placement assist device is in place and a clinician-facing surface that is not in contact with the labia when the catheter placement assist device is in place, and further comprising at least one feature selected from the group consisting of (i) a light mounted on the clinician-facing surface, (ii) swab storage, (iii) a handle on the clinician-facing surface, and (iv) a catheter tip holder to hold the sterile catheter in a location to be readily accessible to the clinician placing the catheter.

4. The catheter placement assist device of claim 3, wherein the handle includes a bendable end to be rested upon a surface when the catheter placement assist device is in place.

5. A catheter placement assist device comprising:
   a pair of wings that meet at a valley, each of the wings having a curved profile;
   a spout protruding from one end of the valley, the spout forming one side of an introital aperture through which a urethral meatus can be optimally visualized;
   a posterior shield protruding from another end of the valley;
   wherein the wings either overlap one another around the introital aperture before terminating, or form a permanent gap adjacent to the introital aperture before terminating;
   wherein an angle a determined for surface points along the wings by a tangent to each surface point of one of the wings and a midline of the wings increases non-linearly from the spout and valley before decreasing to an outside edge of the one of the wings.

6. The catheter placement assist device of claim 5, wherein the wings comprise at least one of a malleable material, an elastic material, and a malleable metallic wire.

7. The catheter placement assist device of claim 5, each of the wings having patient-facing surface that is positioned in contact with an inner side of the labia of a patient when the catheter placement assist device is in place and a clinician-facing surface that is not in contact with the labia when the catheter placement assist device is in place, and further comprising at least one feature selected from the group consisting of (i) a light mounted on the clinician-facing surface, (ii) swab storage, (iii) a handle on the clinician-facing surface, and (iv) a catheter tip holder to hold the sterile catheter in a location to be readily accessible to the clinician placing the catheter.

8. The catheter placement assist device of claim 7, wherein the handle includes a bendable end to be rested upon a surface when the catheter placement assist device is in place.

9. The catheter placement assist device of claim 5, wherein the wings form a permanent gap adjacent to the introital aperture before terminating, wherein the permanent gap is spanned by tape, wherein the tape has a tab for removal of the tape, and wherein the permanent gap has two sides that are at least one of deformable to be closed and always spaced apart.

10. A catheter placement assist device comprising:
    a pair of wings that meet at a valley, each of the wings having a curved profile;
    a spout protruding from one end of the valley, the spout forming one side of an introital aperture through which a urethral meatus can be optimally visualized;
    a posterior shield protruding from another end of the valley;
    wherein the wings either overlap one another around the introital aperture before terminating, or form a permanent gap adjacent to the introital aperture before terminating;
    wherein an angle a determined for surface points along the wings by a tangent to each surface point of one of the wings and a midline of the wings decreases non-linearly from the spout and valley before increasing and then decreasing to an outside edge of the one of the wings.

11. The catheter placement assist device of claim 10, wherein the wings comprise at least one of a malleable material, an elastic material, and a malleable metallic wire.

12. The catheter placement assist device of claim 10, each of the wings having patient-facing surface that is positioned in contact with an inner side of the labia of a patient when the catheter placement assist device is in place and a clinician-facing surface that is not in contact with the labia when the catheter placement assist device is in place, and further comprising at least one feature selected from the group consisting of (i) a light mounted on the clinician-facing surface, (ii) swab storage, (iii) a handle on the clinician-facing surface, and (iv) a catheter tip holder to hold the sterile catheter in a location to be readily accessible to the clinician placing the catheter.

13. The catheter placement assist device of claim 12, wherein the handle includes a bendable end to be rested upon a surface when the catheter placement assist device is in place.

14. The catheter placement assist device of claim 10, wherein the wings form a permanent gap adjacent to the introital aperture before terminating, wherein the permanent gap is spanned by tape, wherein the tape has a tab for removal of the tape, and wherein the permanent gap has two sides that are at least one of deformable to be closed and always spaced apart.

15. A method of using a catheter placement assist device, comprising:
- following a urogenital cleft with a spout and valley of a catheter placement assist device having a pair of wings that meet at the valley, each of the wings having a curved profile, the spout formed at one end of the valley, and a posterior shield extending from the other end of the valley;
- separating first labia minora with the spout, valley, and wings of the catheter placement assist device;
- separating second labia majora with the spout, valley, and wings of the catheter placement assist device;
- covering perineal tissues with a posterior shield of the catheter placement assist device;
- enabling visualization of a urethral meatus through the introital aperture;
- inserting a catheter through the introital aperture into the urethral meatus,
- and molding the wings prior to following the urogenital cleft to account for labial asymmetry.

16. The method of claim 15, and inserting the spout into a vaginal vestibule of a patient.

17. The method of claim 15, and at least one of turning on a light on the catheter placement assist device and removing an antimicrobial swab from a storage location of the catheter placement assist device.

18. The method of claim 15, and at least one of placing the catheter placement assist device using a handle on a clinician-facing surface of the catheter placement assist device that is not in contact with the labia when the catheter placement assist device is in place, removing the catheter placement assist device using the handle of the catheter placement assist device, and resting an end of the handle of the catheter placement assist device on a surface.

19. The method of claim 15, and inserting a sterile urinary catheter through the visualized urethral meatus in the introital aperture.

20. The method of claim 15, and removing the catheter placement assist device by at least one of moving a portion of tubing of an inserted catheter through a space created in a potential gap between overlapping portions of the wings forming the introital aperture, and removing tape from a permanent gap between the wings and moving a portion of tubing of an inserted catheter through the permanent gap between the wings.

* * * * *